US006458401B1

(12) United States Patent
Beauregard et al.

(10) Patent No.: US 6,458,401 B1
(45) Date of Patent: Oct. 1, 2002

(54) PROCESS FOR PRODUCING A POWDER CONTAINING CRYSTALLINE PARTICLES OF MALTITOL

(75) Inventors: Guy Beauregard, Keokuk, IA (US); Mike Jorgenson, Quincy, IL (US); Ben Moser, Keokuk, IA (US); Tom Parady, Hamilton, IL (US)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/713,539

(22) Filed: Nov. 15, 2000

(51) Int. Cl.[7] .......................... A23L 1/236; A21D 10/00
(52) U.S. Cl. ....................... 426/548; 426/453; 426/454; 426/549
(58) Field of Search ........................... 426/548; 127/60, 127/40, 46.1; 568/852

(56) References Cited

U.S. PATENT DOCUMENTS 5,304,388 A       4/1994   Ueno et al.
5,583,215 A      12/1996   Kawashima et al.
6,120,612 A  *    9/2000   Mitsuhashi et al. ........... 127/60
6,344,591 B2 *    2/2002   Leleu et al. ................ 568/852

FOREIGN PATENT DOCUMENTS

EP          0 937 733         8/1999

* cited by examiner

*Primary Examiner*—Leslie Wong
(74) *Attorney, Agent, or Firm*—Henderson & Sturm LLP

(57) ABSTRACT

The invention concerns a process for the manufacture of a powder containing crystalline particles of maltitol, which includes continuously mixing maltitol syrup having a dry matter content of at least 70% by weight and a maltitol content of at least 85% by weight on a dry matter basis, the mixing being effected by simultaneously dispersing the maltitol syrup and maltitol containing seeds into an open rotating receptacle containing maltitol based granules whereby the maltitol syrup and maltitol containing seeds are mixed at the surface of the maltitol based granules contained in the receptacle, collecting maltitol based granules from the receptacle and crystallizing maltitol contained in said granules, the maltitol based granules in the receptacle being maintained in motion by the rotation of the receptacle.

13 Claims, No Drawings

PROCESS FOR PRODUCING A POWDER CONTAINING CRYSTALLINE PARTICLES OF MALTITOL

The invention relates to a process for the continuous manufacture of a powder containing crystalline particles of maltitol.

Maltitol is the result of hydrogenation of maltose.

It is already known how to manufacture crystallized maltitol, for example by inducing the crystallization of said maltitol in a syrup sufficiently rich in this product and sufficiently purified.

The various prior art methods for preparing anhydrous crystals of maltitol or a powder containing crystalline particles of maltitol include molasses separation method, spray drying method, fluid granulating method or block disintegration method.

But all the above methods are disadvantageous in that it is difficult to make the apparatus simple and continuous due to the long time needed to age the crystals.

U.S. Pat. No. 5,304,388 concerns a method for manufacturing a powdery or granular crystalline maltitol.

More precisely, the method comprises adding seed crystals of maltitol at a temperature lower than the melting point of the said seed crystals of maltitol to an aqueous solution of maltitol with 1–15% by weight of moisture content.

But this process needs a step of kneading the mixture in the presence or absence of additives selected from the group consisting of fat, an oil and a surface-active agent, and particularly, makes crucial the step of continuously applying a shearing force to the kneaded mass.

U.S. Pat. No. 5,583,215 concerns a crystalline mixture solid containing maltitol and a process for producing it.

The process requires the supplying of an aqueous solution of maltitol to an extruder provided with elongated cooling and kneading zones, cooling and kneading the aqueous solution of maltitol in the presence of seed crystals to form a maltitol magma, and extruding continuously said magma from a nozzle.

But the process has the disadvantage of requiring the use of an aqueous solution of maltitol having a concentration in the range of 80–98% by weight and a maltitol content in the solid component in the range of 80–99% by weight that has to be supply to the extruder provided with four successive zones that have their temperature precisely controlled.

EP 937,733 focuses on making improvements to these methods for continuous making of maltitol molasses containing crystals.

It describes a manufacturing method comprising continuously supplying an aqueous solution of maltitol to an extruder having a slender kneading and cooling zone, subjecting it to continuous cooling and kneading in the presence of seed crystals to produce a maltitol magma which is continuously extruded from a nozzle.

Subsequent steps of rough disintegration, aging, drying, etc, are also mentioned in relation to producing a final powdery product.

But in this process, the cooling is used to effect crystallization by increasing the degree of supersaturation of the solution. So it is necessary to reduce viscosity by heating the solution having a high concentration of maltitol at a high temperature so that the seed crystals are homogeneously dispersed within a short time.

This process presents the disadvantage of absorbing a lot of power because it needs the formation of a "massecuite", i.e. a seed crystal containing supersaturated substance, having a high concentration of maltitol, up to 98 w/w % of maltitol, and a viscosity that is lowered by supplying heating at high temperature by heating apparatus by means of a jacket using a steam of about 110° C. at a pressure of 142 kPa.

It is also necessary to use this particular heating apparatus for preventing the deterioration of a mixing and dispersing ability as a result of an increase in viscosity due to lowering of the temperature and it is crucial to keep the low viscosity for dispersing and mixing of the seed crystals in a short time.

On the other hand, the process requires another step of disintegration during crystallization that makes the process more complex and time consuming.

Moreover, all the methods known in the prior art present the disadvantage of being expensive, complex and time consuming.

The invention has, as its particular aim, the providing of a process for manufacturing a powder containing crystalline particles of maltitol which are less susceptible to the aforementioned disadvantages and which enables a powder containing crystalline particles of maltitol having desirable properties to be efficiently obtained.

According to the present invention, there is provided a process for the manufacture of crystalline particles of maltitol, that does not need very high concentration of maltitol or any effort undertaken to control or measure precisely the temperature during the granulation/crystallization step.

Moreover, the process of the invention does not involve formation of massecuite, neither application of a shear force or kneading, instead just relying on concurrent coating, agglomeration, and induction of crystallization by allowing the agglomerated mixture mature at a temperature below the melting point of the maltitol, to form solid granules.

According to the present invention, there is provided a process for the manufacture of a powder containing crystalline particles of maltitol, which comprises continuously mixing maltitol syrup having a dry matter content of at least 70% by weight and a maltitol content of at least 85% by weight on a dry matter basis, the mixing being effected by simultaneously dispersing the maltitol syrup and maltitol containing seeds into an open rotating receptacle containing maltitol based granules whereby the maltitol syrup and maltitol containing seeds are mixed at the surface of the maltitol based granules contained in the receptacle, collecting maltitol based granules from the receptacle and crystallizing maltitol contained in said granules, the maltitol based granules in the receptacle being maintained in motion by the rotation of the receptacle.

In carrying out the process of the invention, the maltitol syrup is preferably introduced into the receptacle in a sub-divided form, for example in the form of drops or globules, jets, or bundles of jets.

According to a preferred method of carrying out the abovementioned process, a maltitol syrup, with a content in dry matter of at least 85 weight % is brought to a temperature of at least 80° C. and is continuously mixed in a receptacle with maltitol containing seeds, the seed/syrup ratio, the dimensions, the orientation of the axis of rotation and the speed of rotation of the receptacle being selected so that the product collected from the receptacle appears in the form of granules of an average diameter of from about 500 to 10,000 μm.

The process of the invention may be carried out in an apparatus comprising an open rotating receptacle, with a rotation axis possibly horizontally inclined, means for bringing to an area situated inside the receptacle, above the mass which partially fills it, and dispersing therein some maltitol syrup, preferably sub-divided into the forms referred to above and some maltitol containing seeds and means to ensure the mixing of the maltitol syrup and maltitol-containing seeds on the surface of the moving mass partially filling the receptacle.

The maltitol based granules are collected preferably by overflow at the outlet of the receptacle and may be matured to increase their crystallinity by transferring the granules to a rotating cylinder with dimension characteristics such that the duration of stay of the granules coming from the receptacle is sufficient to ensure crystallization of the maltitol. The granules may then be passed to a dryer to reduce the residual moisture content, and subsequently to a means for grinding and sifting.

In carrying out the process of the invention, a maltitol syrup, of the type available in the trade, that is to say which may contain other polyalcohols such as sorbitol, and the dry matter of which is at least 70%, and having a content in maltitol of at least 85% on a dry matter basis is dispersed at a temperature of about 80° C. inside an open rotating receptacle in the form of an open tank or drum having a substantially flat bottom, the axis of rotation of which may be inclined on a horizontal plan at an angle of from 25 to 450°.

An air atomizing nozzle was advantageously used to spray the aqueous syrup onto the rotating bed maltitol containing seed materials, in the pilot-scale granulator.

As regards the maltitol containing seeds going into the aforesaid mixture and the constituent particles of which serve as crystal maltitol containing seeds, a particle size of about 100 $\mu$m is preferred.

The weight ratio in the mixture made up of maltitol containing seeds and maltitol syrup is about 4/1.

The mixing is effected on the surface of the mass in motion filling the receptacle partially; the motion in question brings to mind that a mass of pills inside a pill making machine and it is found that granules which are bigger and bigger are formed, the largest granules having the tendency to come to the surface of the mass in movement.

The granules of maltitol that are obtained, are then matured to increase their crystallinity.

This stage of maturing can be achieved by keeping the granules moving at a temperature below the melting point of the granules, preferably at a temperature of 5 to 90° C., for from 1 to 20 hours in a current of air.

The granulated product is then dried in order to achieve a residual moisture content of not more than about 2 %.

The granules may then be ground to the required particle size then sorted by sifting ; the particles eliminated by sifting may then advantageously be recycled to the abovementioned receptacle for use as maltitol containing seeds.

The resultant powder containing crystalline particles of maltitol are characterized by the fact that they exhibit a speed of dissolution in water, according to test A, which is less than 3 min.

In order to measure the first characteristics of the powder containing crystalline particles of maltitol in accordance with the invention, namely the time for dissolution, Test A will be carried out. Test A consists in introducing, into 500 ml of demineralized and degassed water maintained at 37° C., and subjected to stirring at 100 rpm, exactly 5 g of a particle size cut of 75 $\mu$m to 150 $\mu$m of the product to be tested.

The dissolution time corresponds to the time necessary, after introduction of the particle size cut, to obtain perfect visual clarity of the mixture thus prepared.

Under these conditions, the powder containing crystalline particles of maltitol in accordance with the invention generally has a rate of dissolution of less than 3 min. The preferred product dissolves in less than 2.0 min.

These times are less than those obtained with other maltitol powders currently marketed.

A second very advantageous property is that the powder containing crystalline particles of maltitol in accordance with the invention exhibit a compression value, according to test B, which is up to about 500 N.

Test B consists in measuring the hardness, expressed in Newtons, of the tablet sample produced on a Carver Press with a 18 kNewtons load applied to a Carver #3619 13 mm pellet die to obtain a tablet containing approximately 0.9 g of powder containing crystalline particles of maltitol in accordance with the invention and 1% magnesium stearate.

The hardness of the tablet is determined in a Dr. SCHLEUNIGER PHARMATRON model 6D tablet tester.

The results show that the powder containing crystalline particles of maltitol in accordance with the invention present a high hardness value.

In order to measure the apparent specific gravity of the powder containing crystalline particles of maltitol in accordance with the invention, Test C will be carried out.

Test C consists in pouring approximately 250 ml of material having a particle size cut of 300 $\mu$m to 850 $\mu$m into a 250 ml graduated cylinder, and the apparent specific gravity values are calculated by dividing the weight of the material by its measured volume.

The performance of the powder containing crystalline particles of maltitol in accordance with the invention is evaluated in shortbread sugar free cookies and deposited oatmeal sugar free cookies.

The following examples illustrate the preparation of the powder containing crystalline particles of maltitol by the use of the process according to the invention.

EXAMPLE 1

A solution having a content of about 89.9% maltitol on a dry matter basis is brought into an evaporation vessel to obtain a maltitol syrup with a content in dry matter of about 90%.

This maltitol syrup is put into a storage tank at a temperature of about 115° C., from which it is continuously taken by means of a pump which ensures its dispersion in the form of globules by means of a nozzle.

Simultaneously with the dispersion of said maltitol syrup, additional seed material is continuously introduced into the pilot granulator to achieve a seed/syrup weight ratio of about 4 parts seed to 1 part maltitol syrup.

The seed is obtained by continuously recirculating a fraction of the solidified material being produced. Particles of any crystalline maltitol solid can be used to supply seed for the initial granulation.

No special efforts are undertaken to control the temperature of the granulator.

The granulator rotates at a speed of about 6.5 revolutions/minute its inclination being 30°, and this permits the obtaining of granules with a mean diameter of about 500 $\mu$m to 10,000 $\mu$m.

After this step of granulation, the said granules are matured by completion of the crystallization in a ripening device (elongated rotating drum).

The matured granules so obtained are submitted to a rough grinding and dried in a fluidized bed using air at about 90° C.

After drying, they appeared in the form of a powder containing approximately 1.8% residual moisture.

At the outlet of the fluidized bed conveyor, the dried powder is led to a conventional grinding plant.

The dried powder is then sifted and a part of it is recycled as maltitol containing seeds to the granulator.

The reminding powder is the powder containing crystalline particles of maltitol according to the invention.

The dissolution rate, as measured according to Test A is of 1 min 50 sec, and the hardness value determined according to Test B is 470 N.

The apparent specific gravity, as measured according to test C, is 0.602 g/ml.

EXAMPLE 2

The performance of the powder containing crystalline particles of maltitol in Example 1 is evaluated in shortbread sugar free cookies and deposited oatmeal sugar free cookies.

MALTISORB® P200 marketed by ROQUETTE FRERES and AMALTY® MR-50 by TOWA are used to produce comparative examples.

The sugar free shortbread cookies and the sugar free oatmeal cookies ingredients are the following.

| SUGAR FREE SHORTBREAD COOKIES | |
|---|---|
| INGREDIENT | Percent |
| Maltitol | 18.00 |
| Shortening (ADM Cookie Bake) | 21.70 |
| Salt | 0.50 |
| Baking Soda | 0.16 |
| Vanilla Flavor (Massey Bourbon) | 0.30 |
| Whole egg | 0.67 |
| Sorbitol P 110 | 2.00 |
| Baking Powder | 0.04 |
| Natural Butter Flavor Bell Flavors OS | 0.04 |
| Caramel Color | 0.06 |
| Water | 8.00 |
| Pastry Flour (Con Agra) | 48.53 |
| | 100.00 |

The procedure is the following
Blend Sorbitol, Maltitol, Shortening, Salt, Baking Soda, Flavor, Egg and Baking Powder at low speed 2 min
Add Butter flavor, Color and water. Mix 1 min at low speed
Add flour and mix 1 min at low speed
Bake at 425° F. for 9 min

| SUGAR FREE OATMEAL COOKIES | |
|---|---|
| INGREDIENT | Percent |
| Maltitol | 18.60 |
| Cookie Bake shortening | 16.00 |
| Eggs | 0.50 |
| Vanilla Flavor (Massey Bourbon) | 0.16 |
| Baking Soda | 0.36 |
| Cinnamon | 0.21 |
| Salt | 0.20 |
| Brown Sugar Flavor | 0.17 |
| Neosorb Sorbitol P110 | 6.80 |
| Quick Oats | 20.40 |
| Pastry Flour (Con Agra) | 29.09 |
| Water | 7.51 |

| SUGAR FREE OATMEAL COOKIES | |
|---|---|
| INGREDIENT | Percent |
| | 100.00 |

The procedure is the following:
Blend Maltitol, sorbitol, shortening, salt, baking soda, egg at low speed 2 min
Add ½ of mixture of brown sugar and vanilla flavor and water. Mix 1 min. at low speed
Add flour and oats and remaining water mixture and mix 1 min at low speed
Batch about 22–23 g per cookie and bake at 425 F. for 9 min.

In shortbread and oatmeal cookies, the powder containing crystalline particles of maltitol of the invention exhibited quicker dissolution, which allows for reduction of mixing time from a total of 6 min to 4 min.

In the shortbread recipe, the dough from this procedure was comparable in texture to dough made with MALTISORB® P200 and was easily processed in a molding process to form cookies of a desired shape and size. Oatmeal cookies made with the powder containing crystalline particles of maltitol of the invention also required less mixing time to achieve the same consistency typical for wire cut or deposited cookies.

No changes are made or required in the baking conditions for either cookie type. Cookies made with the powder containing crystalline particles of maltitol of the invention are slighter than comparable sugar free cookies made with MALTISORB® P200 and AMALTY® R50.

During extended storage, cookies made with the powder containing crystalline particles of maltitol of the invention remained softer than the control cookies made with MALTISORB® P200 and AMALTY® R50, a desired characteristic for products with long shelf life.

What is claimed is:

1. A process for the manufacture of a powder containing crystalline particles of maltitol, which comprises continuously mixing maltitol syrup having a dry matter content of at least 70% by weight and a maltitol content of at least 85% by weight on a dry matter basis, the mixing being effected by simultaneously dispersing the maltitol syrup and maltitol containing seeds into an open rotating receptacle containing maltitol based granules whereby the maltitol syrup and maltitol containing seeds are mixed at the surface of the maltitol based granules contained in the receptacle, collecting maltitol based granules from the receptacle and crystallizing maltitol contained in said granules, the maltitol based granules in the receptacle being maintained in motion by the rotation of the receptacle.

2. A process as claimed in claim 1 in which the maltitol syrup is introduced into the receptacle in a sub-divided form.

3. A process as claimed in claim 2 in which the maltitol syrup is introduced in the forms of drops.

4. A process as claimed in claim 2 in which the maltitol syrup is introduced in the form of jets.

5. A process as claimed in claim 1 in which the axis of rotation of the receptacle is inclined to the horizontal.

6. A process as claimed in claim 1 in which the maltitol based granules are collected by overflow at the outlet of the receptacle.

7. A process according to claim 1 in which granules of a diameter from 150 to 10,000 μm are collected.

8. A process according to claim 1 in which maltitol syrup having a dry matter content of at least 90 weight % is brought to a temperature of at least 80° C. and continuously mixed with maltitol containing seeds, the seed/syrup ratio, the dimensions, the orientation of the axis of rotation and the speed of rotation of the receptacle being selected so that the product collected from the receptacle appears in the form of granules of a diameter of from 150 to 10,000 μm.

9. A process according to claim 8, in which the seed/syrup ratio is not more than about 4/1.

10. A process according to claim 1 in which the receptacle is in the form of an open tank or drum having a substantially flat bottom.

11. A process according to claim 10, in which the axis of rotation of the receptacle makes an angle of from 25 to 45° to the horizontal.

12. A process according to claim 1 in which the collected maltitol granules are matured in order to increase their crystallinity by maintaining the granules at a temperature of from 5 to 90° C. for from 1 to 20 hours while keeping the granules moving in a current of air.

13. A process according to claim 12 in which the collected matured maltitol granules are ground and dried in order to achieve a residual moisture content of not more than about 2%.

* * * * *